United States Patent
Ioka et al.

(10) Patent No.: US 10,863,149 B2
(45) Date of Patent: Dec. 8, 2020

(54) IMAGE PROCESSING APPARATUS, IMAGE PROCESSING METHOD, AND COMPUTER READABLE RECORDING MEDIUM

(71) Applicant: OLYMPUS CORPORATION, Tokyo (JP)

(72) Inventors: Ken Ioka, Hachioji (JP); Wataru Oniki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/391,159

(22) Filed: Apr. 22, 2019

(65) Prior Publication Data

US 2019/0253675 A1 Aug. 15, 2019

Related U.S. Application Data

(63) Continuation of application No. PCT/JP2016/086633, filed on Dec. 8, 2016.

(51) Int. Cl.
*H04N 5/225* (2006.01)
*H04N 9/04* (2006.01)
(Continued)

(52) U.S. Cl.
CPC ..... *H04N 9/04515* (2018.08); *A61B 1/00009* (2013.01); *A61B 1/0638* (2013.01);
(Continued)

(58) Field of Classification Search
CPC combination set(s) only.
See application file for complete search history.

(56) References Cited

U.S. PATENT DOCUMENTS

| 6,943,837 B1 * | 9/2005 | Booth, Jr. | H04N 5/3537 348/223.1 |
| 2012/0154566 A1 * | 6/2012 | Kaku | G02B 23/2461 348/68 |

(Continued)

FOREIGN PATENT DOCUMENTS

| JP | 2005198794 A | 7/2005 |
| JP | 2012125461 A | 7/2012 |

(Continued)

OTHER PUBLICATIONS

International Search Report (ISR) dated Mar. 7, 2017 issued in International Application No. PCT/JP2016/086633.

(Continued)

*Primary Examiner* — Md N Haque
(74) *Attorney, Agent, or Firm* — Holtz, Holtz & Volek PC

(57) ABSTRACT

An image processing apparatus includes a processor configured to execute: acquiring image data; generating first interpolation image data associated with light having a red wavelength band, second interpolation image data associated with light having a green wavelength band, third interpolation image data associated with light having a blue wavelength band, and fourth interpolation image data associated with narrow band light; performing a color space conversion process for converting each of the first to the third interpolation image data to a luminance component and a color difference component; extracting a first specific frequency component included in the fourth interpolation image data; combining the converted luminance component with the extracted first specific frequency component; and generating color image data based on a combination result obtained by the combining and based on the color difference component.

6 Claims, 13 Drawing Sheets

(51) Int. Cl.
*A61B 1/06* (2006.01)
*A61B 1/00* (2006.01)
*H04N 9/083* (2006.01)
*G06T 1/00* (2006.01)
*H04N 9/07* (2006.01)

(52) U.S. Cl.
CPC ............... *G06T 1/00* (2013.01); *H04N 9/07* (2013.01); *H04N 9/083* (2013.01)

(56) References Cited

U.S. PATENT DOCUMENTS

| | | | | |
|---|---|---|---|---|
| 2014/0044359 | A1* | 2/2014 | Rousson | G06K 9/4604 |
| | | | | 382/197 |
| 2014/0328538 | A1* | 11/2014 | Kim | H04N 9/045 |
| | | | | 382/167 |
| 2015/0146067 | A1* | 5/2015 | Roh | H04N 5/345 |
| | | | | 348/308 |
| 2017/0325658 | A1 | 11/2017 | Ioka et al. | |
| 2019/0124258 | A1* | 4/2019 | Ioka | A61B 1/00009 |

FOREIGN PATENT DOCUMENTS

| | | |
|---|---|---|
| JP | 5501210 B2 | 5/2014 |
| WO | 2016129062 A1 | 8/2016 |

OTHER PUBLICATIONS

Written Opinion dated Mar. 7, 2017 issued in International Application No. PCT/JP2016/086633.

\* cited by examiner $$F1 \begin{pmatrix} -1 & -1 & -1 \\ -1 & 9 & -1 \\ -1 & -1 & -1 \end{pmatrix}$$

IMAGE PROCESSING APPARATUS, IMAGE PROCESSING METHOD, AND COMPUTER READABLE RECORDING MEDIUM

CROSS-REFERENCE TO RELATED APPLICATION

This application is a continuation of International Application No. PCT/JP2016/086633, filed on Dec. 8, 2016, the entire contents of which are incorporated herein by reference.

BACKGROUND

The present disclosure relates to an image processing apparatus, an image processing method, and a computer readable recording medium.

In recent years, as an observation system using endoscopes, there is a known narrow band light observation system using illumination light (hereinafter, referred to as "special light") consists of two pieces of narrow band light included in blue and green wavelength bands.

As endoscopes used in such a narrow band light observation system, there is a known technology for observing, using a single observation image, a capillary blood vessel, a fine pattern of the mucous membrane, and the like that are present on the surface layer of a mucous membrane of a living body by combining pieces of information on a special light observation image obtained by performing imaging using special light with a normal light observation image obtained by performing imaging using white light (see Japanese Patent No. 5501210). With this technology, feature information, such as a capillary blood vessel and a fine pattern of the mucous membrane, is extracted from the special light observation image by using a high-pass filter, a band-pass filter, and the like, and then a combined image is generated by combining the extracted feature information with a normal light observation image.

SUMMARY

According to one aspect of the present disclosure, there is provided an image processing apparatus comprising a processor comprising hardware, the processor being configured to execute: acquiring image data generated by an image sensor formed by a predetermined array pattern using a first pixel that receives light having a red wavelength band, a second pixel that receives light having a green wavelength band, a third pixel that receives light having a blue wavelength band, and a fourth pixel that receives narrow band light having a wavelength band that is narrower than at least any of the red, green, and blue wavelength bands; generating, by performing a demosaicing process for interpolating a pixel value on the acquired image data, first interpolation image data associated with the light having the red wavelength band, second interpolation image data associated with the light having the green wavelength band, third interpolation image data associated with the light having the blue wavelength band, and fourth interpolation image data associated with the narrow band light; performing a color space conversion process for converting each of the first interpolation image data, the second interpolation image data, and the third interpolation image data to a luminance component and a color difference component; extracting a first specific frequency component included in the fourth interpolation image data; combining the converted luminance component with the extracted first specific frequency component; and generating color image data based on a combination result obtained by the combining and based on the color difference component.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
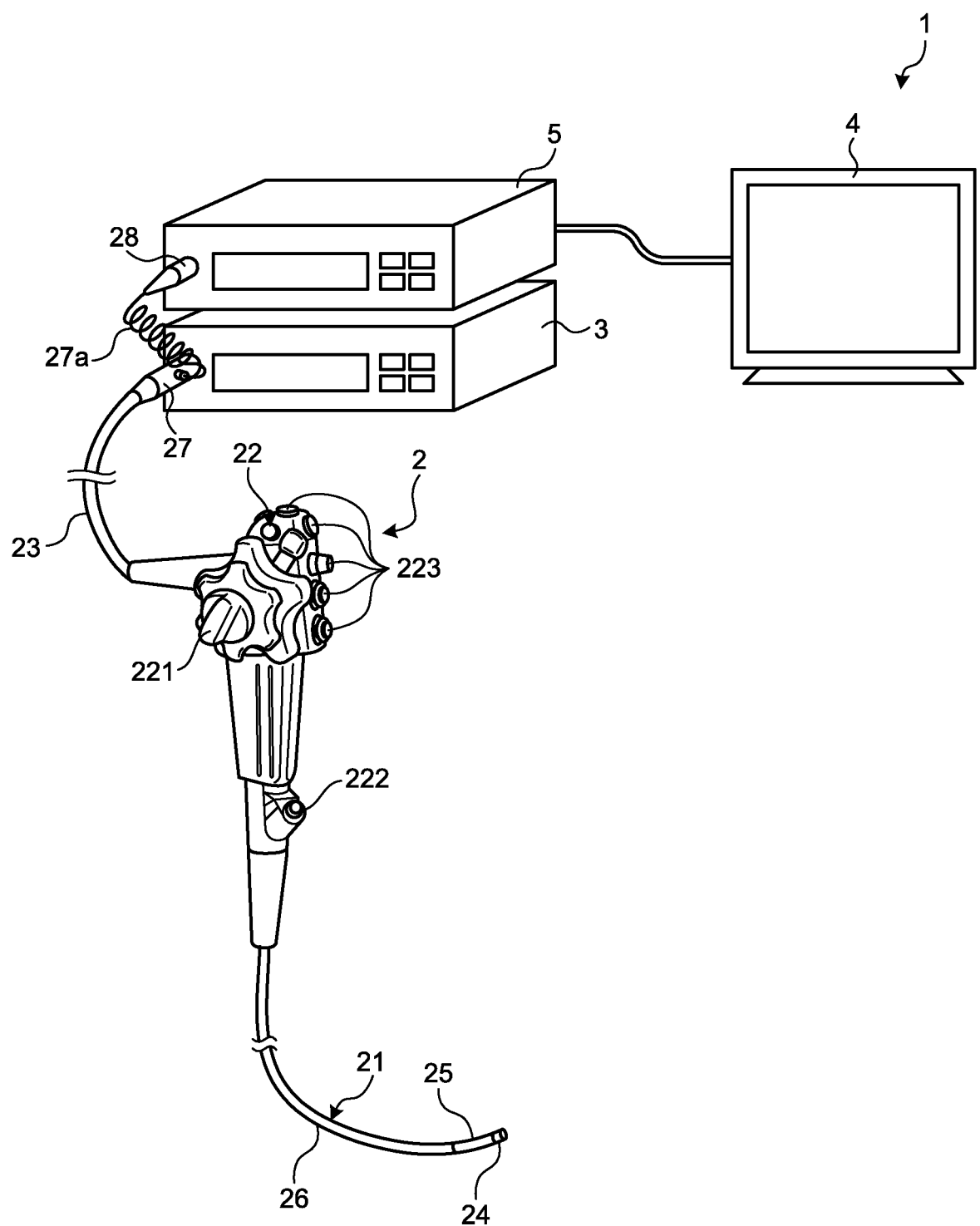
FIG. 1 is a diagram schematically illustrating the overall configuration of an endoscope system of a first embodiment.

In the following, modes for carrying out the present disclosure (hereinafter, referred to as an "embodiment") will be described. In the embodiment, a description will be given by using, as an example, an endoscope system for medical use that captures images inside a body cavity of a subject, such as a patient, and displays the images. Furthermore, the present disclosure is not limited to the embodiments described below. Furthermore, in the drawings, components that are identical to those in embodiments are assigned the same reference numerals.

First Embodiment

Configuration of Endoscope System

FIG. 1 is a diagram schematically illustrating the overall configuration of an endoscope system of a first embodiment. An endoscope system 1 illustrated in FIG. 1 includes an endoscope 2 that captures images of an interior of a subject by being inserted into a body cavity of a subject; a light source device 3 that generates illumination light emitted from the distal end of the endoscope 2; a display device 4 that displays an image associated with image data generated by the endoscope 2 by capturing images; and a processor 5 that displays, on the display device 4, an image by performing predetermined image processing on the image data generated by the endoscope 2 capturing the image and that performs overall control of the entire of the endoscope system 1.

The endoscope 2 includes an insertion portion 21 having a flexible narrow tip shape; an operating unit 22 that is connected on the proximal end side of the insertion portion 21 and that receives an input of various operation signals; and a universal cord 23 that extends in a direction that is different from the direction in which the insertion portion 21 extends from the operating unit 22 and that has various built-in cables connected to the processor 5 and the light source device 3.

The insertion portion 21 includes a distal end portion 24 that is provided with a built-in imaging device (imaging unit) that will be described later; a bending portion 25 that is freely bendable formed by a plurality of bending sections; and a flexible tube portion 26 that has a flexible elongated shape and that is connected to the proximal end side of the bending portion 25.

The operating unit 22 includes a bending knob 221 that bends the bending portion 25 in the vertical direction and the horizontal direction; a treatment instrument insertion portion 222 in which an treatment instrument, such as biological forceps, a laser scalpel, or an examination probe, is inserted into the body cavity; and a plurality of switches 223 that is an operation input unit used to input an operation indication signal of, in addition to the light source device 3 and the processor 5, peripheral equipment, such as an air supply means, a water supply means, and a gas supply means. The treatment instrument inserted from the treatment instrument insertion portion 222 is output from an opening portion (not illustrated) via the distal end portion 24.

The universal cord 23 includes therein at least a light guide and an assembled cable. The universal cord 23 includes a connector portion 27 that can be freely inserted to and removed from the light source device 3. The connector portion 27 includes an electricity connector portion 28 that is provided with a coil shaped elongated coil cable 27a and that can be freely inserted to and removed from the processor 5 at the projection end portion of the coil cable 27a. The connector portion 27 is formed therein by using a field programmable gate array (FPGA).

The light source device 3 is formed by using, for example, a halogen lamp, a white light emitting diode (LED), or the like. The light source device 3 irradiates, under the control of the processor 5, illumination light from the distal end side of the insertion portion of the endoscope 2 towards an object.

The display device 4 displays, under the control of the processor 5, the image, which is associated with an image signal that has been subjected to image processing by the processor 5, and various kinds of information related to the endoscope system 1. The display device 4 is formed by using a display panel, such as a liquid crystal panel or an organic electro luminescence (EL) panel.

The processor 5 performs predetermined image processing on the RAW image data input from the endoscope 2 and then outputs the processed image data to the display device 4. The processor 5 is constituted by using a central processing unit (CPU) or the like.

Figure 2:
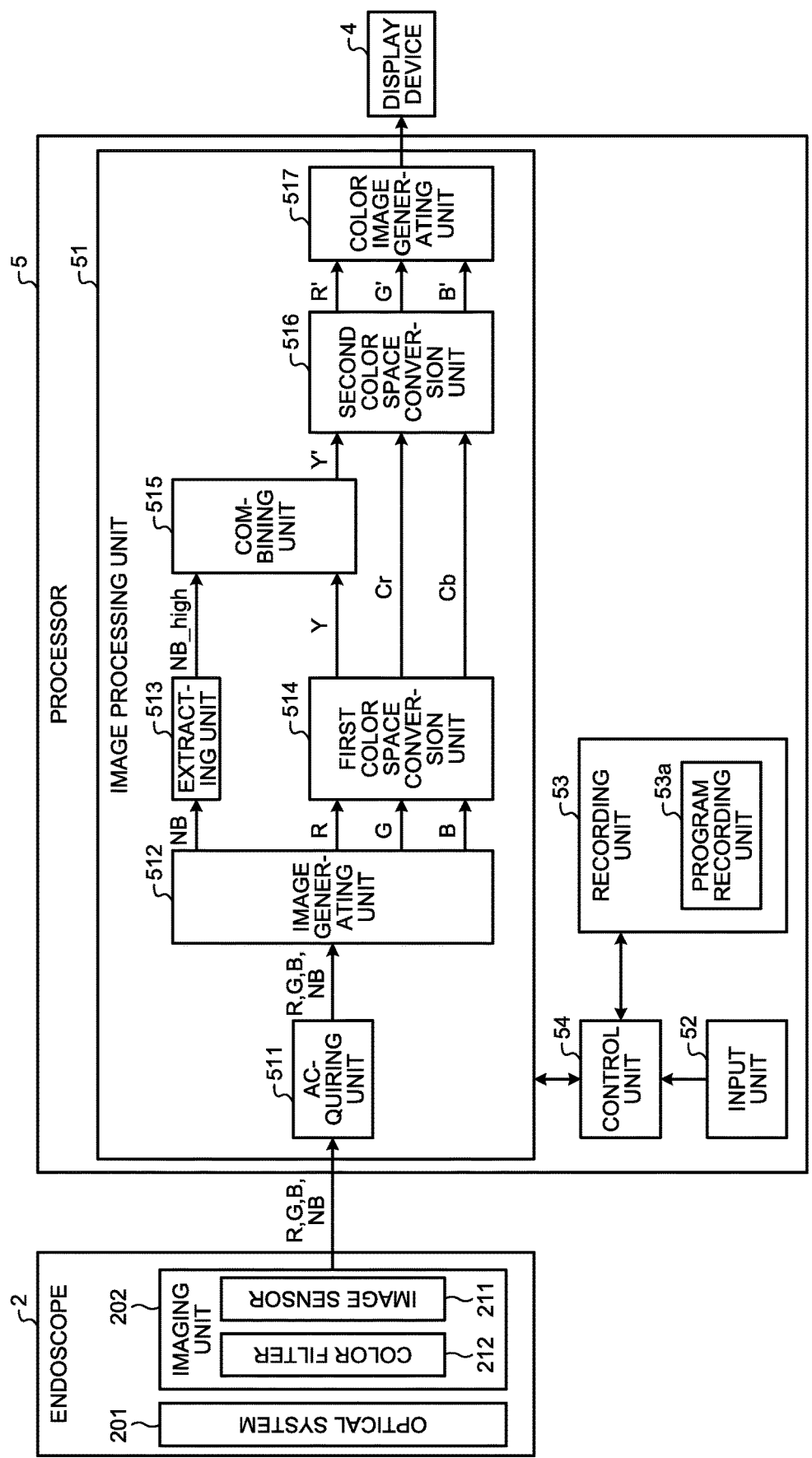
FIG. 2 is a block diagram illustrating the function of a relevant part of the endoscope system according to the first embodiment.

In the following, a function of a relevant part of the endoscope system 1 will be described. FIG. 2 is a block diagram illustrating the function of a relevant part of the endoscope system 1. Each of the units included in the endoscope system 1 and an electrical signal path in the endoscope system 1 will be described in detail with reference to FIG. 2.

Configuration of Endoscope

First, a configuration of the endoscope 2 will be described.

As illustrated in FIG. 2, the endoscope 2 includes an optical system 201 and an imaging unit 202.

The optical system 201 receives light reflected from the illumination light emitted by the light source device 3 on an imaging surface of the imaging unit 202 and forms an object image. The optical system 201 is formed by using a single or a plurality of lenses, prisms, and the like.

The imaging unit 202 generates, under the control of the processor 5, image data (RAW image data) of an object by receiving an object image formed on a light-receiving surface by the optical system 201 and performing photoelectric conversion and outputs the generated image data to the processor 5. Specifically, the imaging unit 202 captures an image of the subject at a reference frame rate, such as the frame rate of, for example, 60 fps, and generates the image data of the subject. The imaging unit 202 includes an image sensor 211 and a color filter 212.

The image sensor 211 is formed by using an imaging sensor, such as a charge coupled device (CCD) or a complementary metal oxide semiconductor (CMOS), that performs photoelectric conversion on light received by a plurality of two-dimensionally arrayed pixels and that generates an electrical signal.

The color filter 212 is formed by using a filter unit that includes a wide-band filter R that transmits light having a red wavelength band, a wide-band filter G that transmits light having a green wavelength band, a wide-band filter B that transmits light having a blue wavelength band, and a narrow-band filter NB that transmits light having a wavelength band that is the blue wavelength band and that is narrower than the blue wavelength band. The color filter 212 is formed by arranging the filter unit so as to be associated with the pixels of the image sensor 211.

Figure 3:
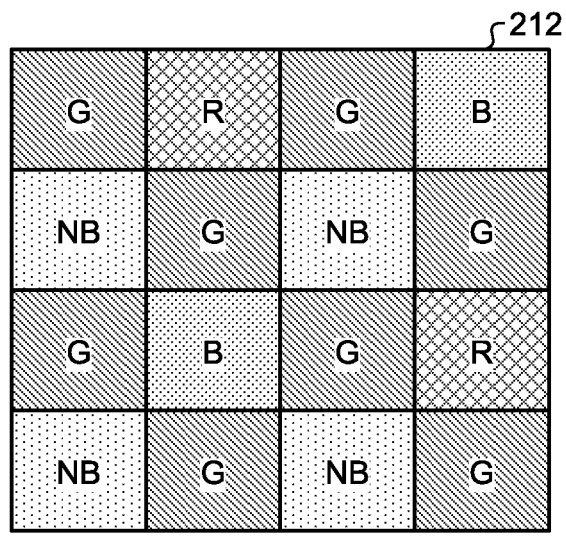
FIG. 3 is a diagram schematically illustrating a configuration of a color filter according to the first embodiment.

FIG. 3 is a diagram schematically illustrating a configuration of the color filter 212. As illustrated in FIG. 3, the color filter 212 is formed by using a filter unit formed of a predetermined array pattern that has, as a single set, two wide-band filters R each of which transmits a red component, eight wide-band filters G each of which transmits a green component, two wide-band filters B each of which transmits a blue component, and four narrow-band filters NB each of which transmits light having a narrow band. The color filter 212 is arranged at the position associated with one of the plurality of pixels of the image sensor 211 in which each of the filters forming the array pattern described above are two dimensionally arrayed. Here, light having a narrow band according to the first embodiment is blue narrow band light (390 to 445 nm) used for observing a capillary blood vessel on the surface layer of a mucous membrane. The image data generated by the image sensor 211 using the color filter 212 formed in this way is converted to a color image by being subjected to predetermined image processing by the processor 5, which will be described later.

Figure 4:
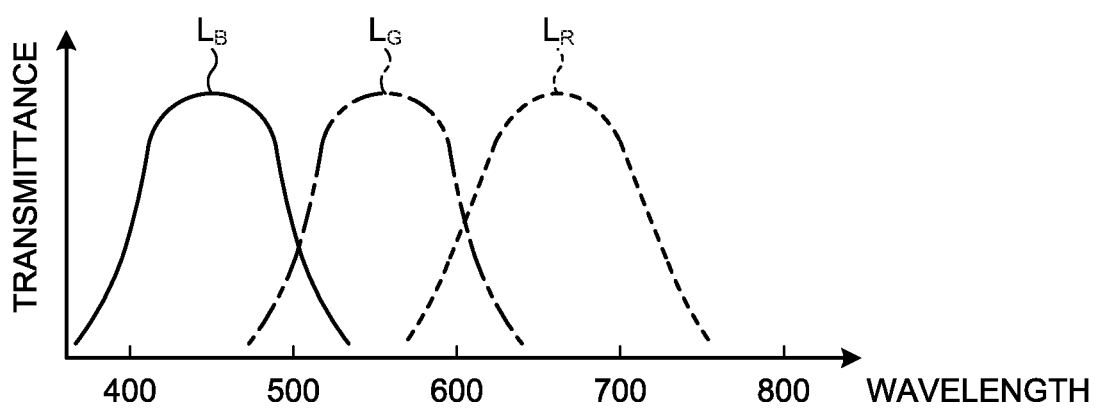
FIG. 4 is a diagram illustrating the relationship between the transmittance and the wavelength of each of the wide-band filters constituting the color filter according to the first embodiment.
Figures 5, 6:
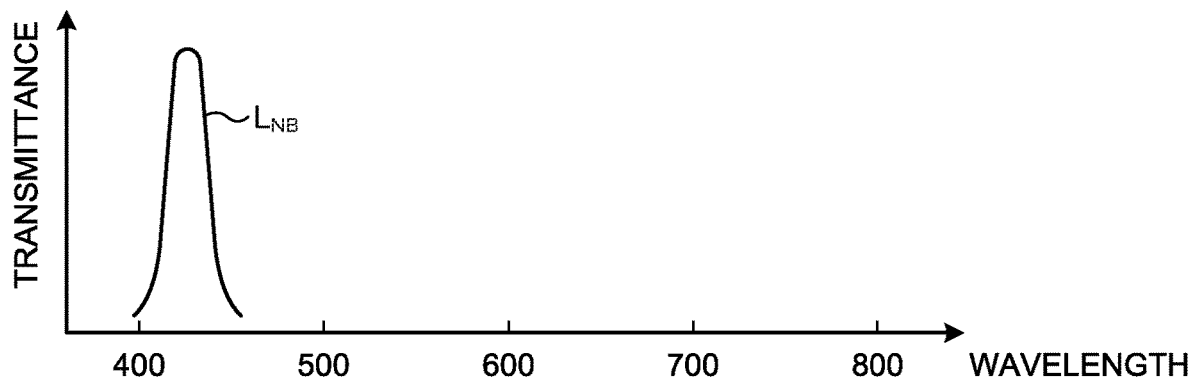
FIG. 5 is a diagram illustrating the relationship between the transmittance and the wavelength of a narrow-band filter NB constituting the color filter according to the first embodiment.
FIG. 6 is a diagram schematically illustrating the characteristic of a filter constituting an extracting unit according to the first embodiment.

FIG. 4 is a diagram illustrating the relationship between the transmittance and the wavelength of each of the wide-band filters constituting the color filter 212. FIG. 5 is a diagram illustrating the relationship between the transmittance and the wavelength of the narrow-band filter NB constituting the color filter. In FIG. 4 and FIG. 5, the horizontal axis represents the wavelength (nm) and the vertical axis represents the transmittance. Furthermore, in FIG. 4, a curve $L_B$ represents the relationship between the transmittance and the wavelength of the wide-band filter B, a curve $L_G$ represents the relationship between the transmittance and the wavelength of the wide-band filter G, and a curve $L_B$ represents the relationship between the transmittance and the wavelength of the wide-band filter R. Furthermore, in FIG. 5, a curve $L_{NB}$ represents the relationship between the transmittance and the wavelength of the narrow-band filter NB. Furthermore, in FIG. 5, a description will be given of a case in which the peak wavelength of the narrow-band filter NB is present in the range between 390 nm and 445 nm.

As illustrated in FIG. 4 and FIG. 5, the spectral characteristic of the narrow-band filter NB is that the wavelength band thereof is included in a wavelength band of the wide-band filter B and is narrower than that of the wide-band filter B. In a description below, pixels formed by arranging the wide-band filter R is referred to as an R pixel (a first pixel), pixels formed by arranging the wide-band filter G is referred to as a G pixel (a second pixel), pixels formed by arranging the wide-band filter B is referred to as a B pixel (a third pixel), and pixels formed by arranging the narrow-band filter NB are referred to as an NB pixel (a fourth pixel).

Configuration of Processor

In the following, a configuration of the processor 5 will be described.

The processor 5 includes, as illustrated in FIG. 2, an image processing unit 51, an input unit 52, a recording unit 53, and a control unit 54.

The image processing unit 51 is constituted by using a graphics processing unit (GPU), a field programmable gate array (FPGA), or the like. The image processing unit 51 acquires image data from the endoscope 2, performs predetermined image processing on the acquired image data, and outputs the processed imaged data to the display device 4. The image processing unit 51 includes an acquiring unit 511, an image generating unit 512, an extracting unit 513, a first color space conversion unit 514, a combining unit 515, a second color space conversion unit 516, and a color image generating unit 517. Furthermore, in the first embodiment, the image processing unit 51 functions as an image processing apparatus.

The acquiring unit 511 acquires the image data generated by the endoscope 2 by capturing an image and then outputs the acquired image data to the image generating unit 512. Specifically, the acquiring unit 511 acquires, from the image sensor 211 the pixel value of each of the R pixel, the G pixel, the B pixel, and the NB pixel (a pixel value R, a pixel value G, a pixel value B, and a pixel value NB) constituting an image that is associated with the image data generated by the endoscope 2 and then outputs each of the acquired pixel values of the pixels to the image generating unit 512.

The image generating unit 512 performs, based on the pixel value of each of the pixels (each channel) that have been input from the acquiring unit 511, a known demosaicing process for interpolating the pixel value of the pixel in which the pixel value has been lost, whereby the image generating unit 512 generates each of an R image (first interpolation image data) associated with light having a red wavelength band, a G image (second interpolation image data) associated with light having a green wavelength band, a B image (third interpolation image data) associated with light having a blue wavelength band, and an NB image (fourth interpolation image data) associated with narrow band light. The image generating unit 512 outputs the R image, the G image, and the B image to the first color space conversion unit 514 and also outputs the NB image to the extracting unit 513.

The extracting unit 513 extracts a first specific frequency component from the NB image that is a narrow band image input from the image generating unit 512 and then outputs the extracted first specific frequency component to the combining unit 515. Specifically, the extracting unit 513 extracts, from the NB image, a high frequency component that is higher than a predetermined threshold. More specifically, as illustrated in FIG. 6, the extracting unit 513 extracts, with respect to the pixel value of each of the pixels constituting the NB pixel, by using, for example, a 3×3 high-pass filter F1, a high frequency component NB high included in the NB image as the feature component of the NB image and then outputs the extracted high frequency component to the combining unit 515. Furthermore, the extracting unit 513 does not always use the 3×3 high-pass filter and may also appropriately change the high-pass filter to, for example, a 4×4 or a 5×5 high-pass filter. Of course, the extracting unit 513 may also be formed by using a plurality of filters in combination.

The first color space conversion unit 514 performs a known color space conversion process, for example, an YCrCb conversion process, for converting the R image, the G image, and the B image input from the image generating unit 512 to a luminance component Y, a color difference component Cr, and a color difference component Cb; outputs the luminance component Y to the combining unit 515; and outputs the color difference component Cr and the color difference component Cb to the second color space conversion unit 516.

The combining unit 515 combines the high frequency component NB_high that has been input from the extracting unit 513 with the luminance component Y that has been input from the first color space conversion unit 514 and then outputs the combined luminance component X' (Y'=Y$_+$NB high) to the second color space conversion unit 516.

The second color space conversion unit 516 performs a known color space conversion process, for example, an RGB conversion process on the luminance component Y' that has been input from the combining unit 515, the color difference component Cr and the color difference component Cb that have been input from the first color space conversion unit 514, thereby generating each of a new observation image R', a new observation image G', and a new observation image B° in each of which a feature component of the narrow band image is added to the wide band image. The second color space conversion unit 516 outputs the observation image R', the observation image G', and the observation image B' to the color image generating unit 517.

The color image generating unit 517 generates color image data based on the observation image R', the observation image G', and the observation image B' that have been input from the second color space conversion unit 516 and then outputs the generated color image data to the display device 4. Specifically, the color image generating unit 517 generates a color image by combining the pixel value of each of the pixels constituting the R' image, the pixel value of each of the pixels constituting the G' image, and the pixel value of each of the pixels constituting the B' image and then outputs the generated color image to the display device 4.

The input unit 52 is constituted by using a button, a switch, or the like and receives an input of an indication signal that indicates various processes performed by the endoscope system 1 and a change signal that changes parameters or the like.

The recording unit 53 is constituted by using a read only memory (ROM), a random access memory (RAM), and the like and records the image data generated by the endoscope 2, the programs executed by the endoscope system 1. Furthermore, the recording unit 53 includes a program recording unit 53a that records the programs executed by the endoscope system 1.

The control unit 54 is constituted by using a CPU or the like and performs overall control each of the units that constitute the endoscope system 1. The control unit 54 controls an emission timing of illumination light output from the light source device 3, an imaging timing of the imaging unit 202 in the endoscope 2, and the like.

Process Performed by Processor

Figure 7:
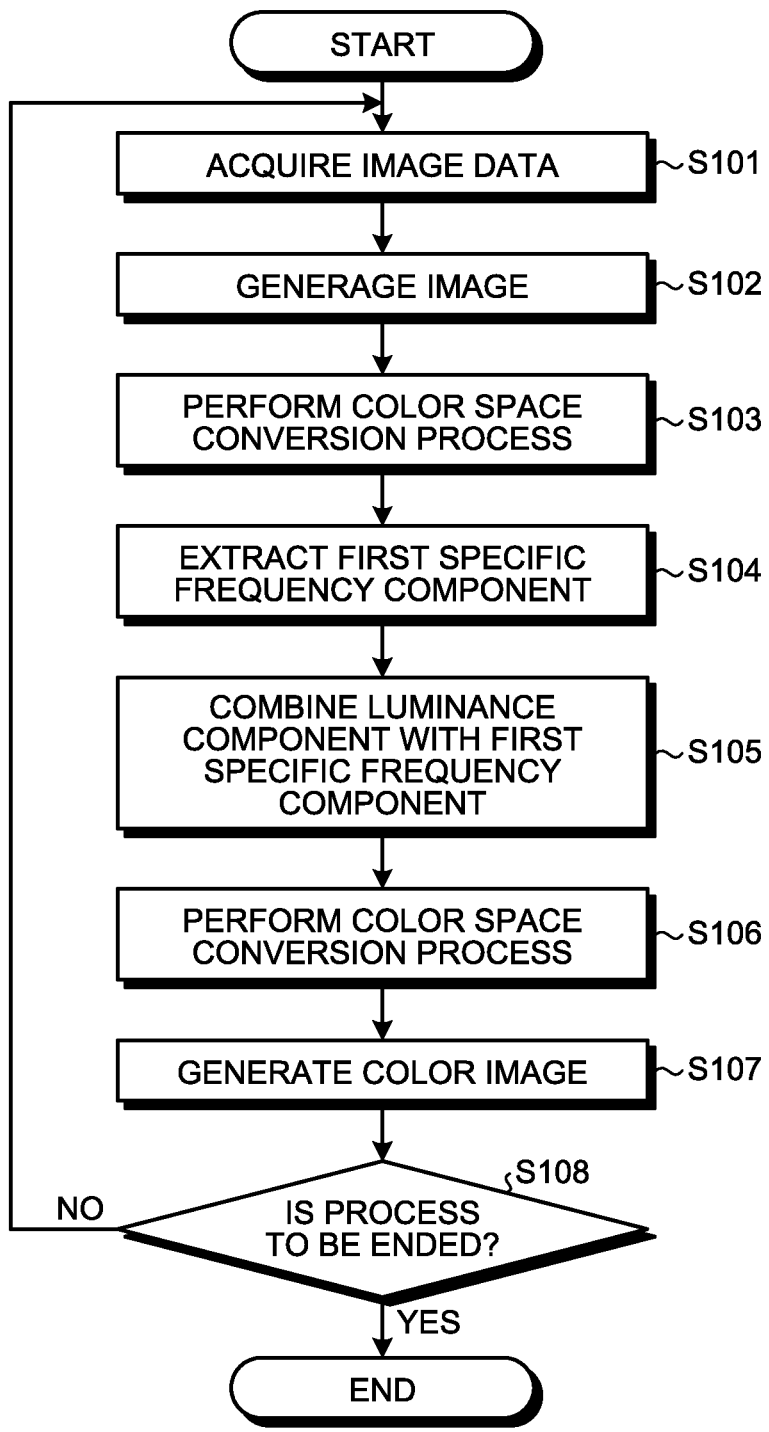
FIG. 7 is a flowchart illustrating the outline of a process performed by a processor according to the first embodiment.

In the following, the process performed by the processor 5 will be described. FIG. 7 is a flowchart illustrating the outline of the process performed by the processor 5.

As illustrated in FIG. 7, first, the acquiring unit 511 acquires image data from the endoscope 2 (Step S101).

Subsequently, the image generating unit 512 generates an image of each color by performing the demosaicing process based on the pixel value of each of the pixels input from the acquiring unit 511 (Step S102).

Then, the first color space conversion unit 514 performs the color space conversion process on the R image, the G image, and the B image that have been input from the image generating unit 512 (Step S103). Specifically, the first color space conversion unit 514 performs the YCrCb conversion process on the R image, the G image, and the B image that have been input from the image generating unit 512 for converting the images to the luminance component Y, the color difference component Cr, and the color difference component Cb, respectively.

Subsequently, the extracting unit 513 extracts the first specific frequency component from the NB image that is the narrow band image input from the image generating unit 512 (Step S104). Specifically, the extracting unit 513 extracts, with respect to the pixel value of each of the pixels constituting the NB pixel, by using the high-pass filter F1 described above illustrated in FIG. 6, the high frequency component NB_high of the NB image as the feature component of the NB image.

Then, the combining unit 515 combines the luminance component Y that has been input from the first color space conversion unit 514 with the first specific frequency component that has been input from the extracting unit 513 (Step S105). Specifically, the combining unit 515 combines the luminance component Y that has been input form the first color space conversion unit 514 to the high frequency component NB_high that is the feature component of the NB image that has been input from the extracting unit 513.

Subsequently, the second color space conversion unit 516 performs the color space conversion process for converting the luminance component Y' that has been input from the combining unit 515 and the color difference component Cr and the color difference component Cb that have been input from the first color space conversion unit 514 to RGB (Step S106).

Then, the color image generating unit 517 generates a color image based on the observation image R', the observation image G', and the observation image B' that have been input from the second color space conversion unit 516 (Step S107).

Subsequently, if an indication signal that indicates the end of the examination performed by the endoscope system 1 has been input (Yes at Step S108), the processor 5 ends the process. In contrast, if an indication signal that indicates the end of the examination performed by the endoscope system 1 has not been input (No at Step S108), the processor 5 returns to Step S101 described above.

According to the first embodiment described above, even if feature information on the special light observation image is combined with the normal light observation image, it is possible to prevent a change in the tone of the combined image.

Furthermore, according to the first embodiment, even when the normal light observation image and the special light observation image are combined, it is possible to acquire a new observation image in which the contrast of the special light image is high.

Furthermore, in the first embodiment, the combining unit 515 may also combine the luminance component Y, which has been input from the first color space conversion unit 514, with the value, which is obtained by multiplying a weighting factor α that has been input by the input unit 52 by the high frequency component NB high of the NB image (Y'=Y+α× NB high).

Furthermore, in the first embodiment, the blue narrow band light (390 to 445 nm) has been described as an example; however, the green narrow band light (530 to 550 nm) may also be used for enhancing a thick blood vessel in a deep portion.

Modification of First Embodiment

In the following, a modification of the first embodiment will be described. The modification of the first embodiment is different from the first embodiment described above in that a configuration of an extracting unit 513 is different. In a description below, only the configuration of an extracting unit according to the modification of the first embodiment will be described. Furthermore, components that are identical to those in the endoscope system 1 according to the first embodiment are assigned the same reference numerals and descriptions thereof will be omitted.

Figures 8, 9:
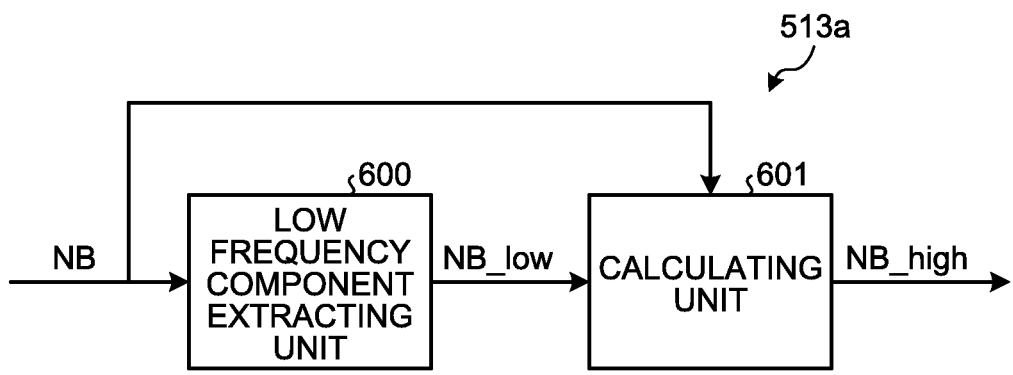
FIG. 8 is a diagram schematically illustrating a configuration of an extracting unit according to a modification of the first embodiment.
FIG. 9 is a diagram schematically illustrating the characteristic of a filter constituting an extracting unit according to the modification of the first embodiment.

FIG. 8 is a diagram schematically illustrating a configuration of the extracting unit according to the modification of the first embodiment. An extracting unit 513a illustrated in FIG. 8 includes a low frequency component extracting unit 600 and a calculating unit 601.

The low frequency component extracting unit 600 extracts a low frequency component NB_low from the NB image that is a narrow band image. The low frequency component extracting unit 600 is formed by using, for example, a 5×5 low-pass filter F2 illustrated in FIG. 9.

The calculating unit 601 calculates the high frequency component NB_high that is the first specific frequency component from the NB image that is the narrow band image by subtracting the low frequency component NB_low, which has been extracted by the low frequency component extracting unit 600, from the NB image that is the narrow band image.

With the modification of the first embodiment described above, similarly to the first embodiment described above, even when the feature information on a special light observation image is combined with a normal light observation image, it is possible to prevent a change in the tone of the combined image.

Second Embodiment

In the following, a second embodiment will be described. A configuration of an endoscope system according to the second embodiment is different from that of the endoscope system 1 according to the first embodiment described above. Specifically, a configuration of a processor according to the second embodiment is different from the processor 5 according to the first embodiment. Furthermore, the process performed by the processor in the endoscope system according to the second embodiment is different from that performed by the processor 5 according to the first embodiment described above. In a description below, a configuration of the endoscope system according to the second embodiment will be described and then a process performed by the processor will be described. Furthermore, components that are identical to those in the endoscope system 1 according to the first embodiment are assigned the same reference numerals and descriptions thereof will be omitted.

Configuration of Endoscope System

Figure 10:
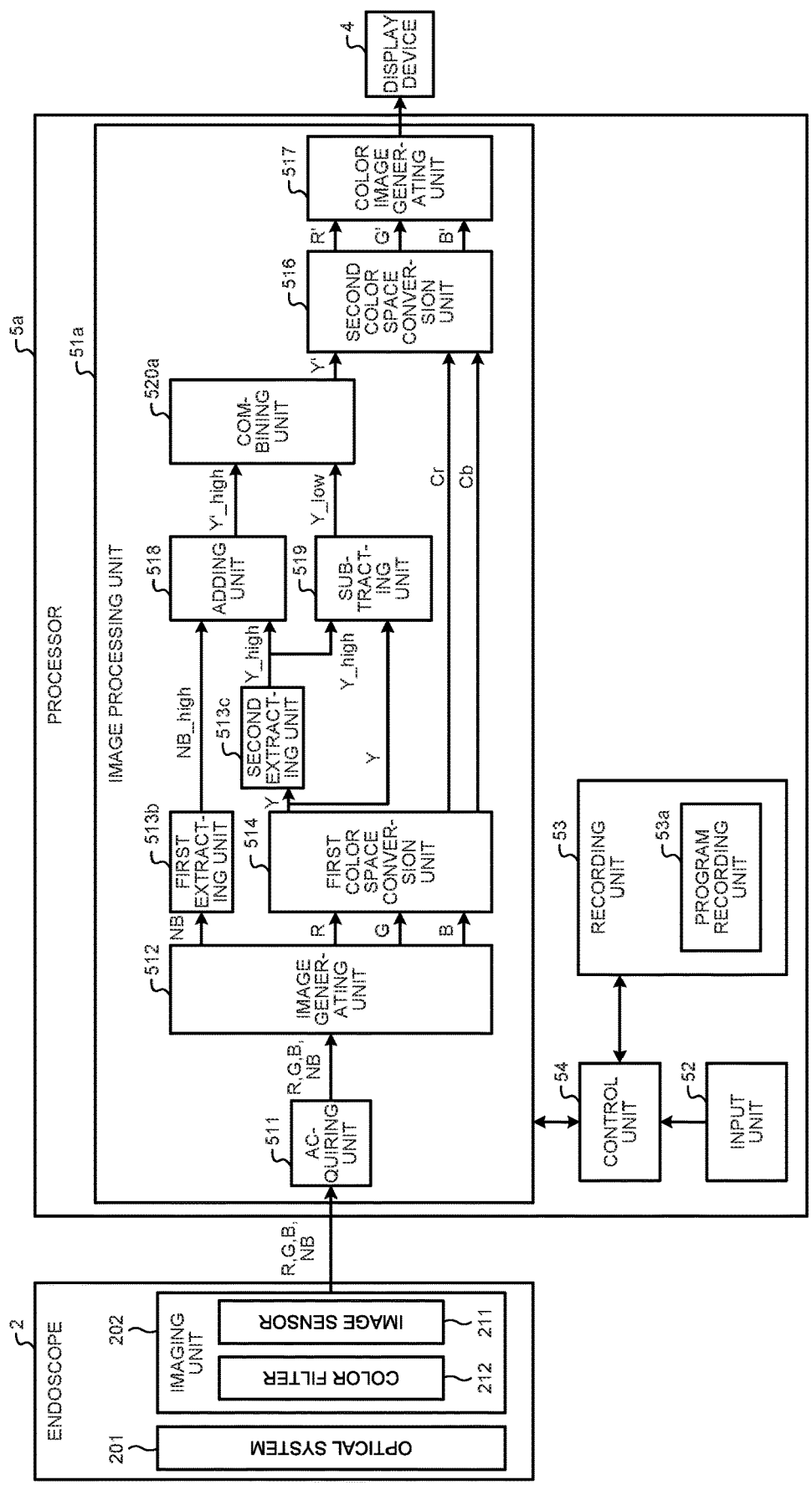
FIG. 10 is a block diagram illustrating the function of a relevant part of an endoscope system according to a second embodiment.

FIG. 10 is a block diagram illustrating a function of a relevant part in the endoscope system according to the second embodiment. An endoscope system 1a illustrated in FIG. 10 includes a processor 5a instead of the processor 5 included in the endoscope system 1 according to the first embodiment described above.

Configuration of Processor

The processor 5a illustrated in FIG. 10 includes an image processing unit 51a instead of the image processing unit 51 according to the first embodiment described above.

The image processing unit 51a is constituted by using a GPU, an FPGA, or the like; acquires image data from the endoscope 2; performs predetermined image processing on the acquired image data; and outputs the processed image data to the display device 4. The image processing unit 51a includes the acquiring unit 511, the image generating unit 512, a first extracting unit 513b, a second extracting unit 513c, the first color space conversion unit 514, an adding unit 518, a subtracting unit 519, a combining unit 520a, the second color space conversion unit 516, and the color image generating unit 517. Furthermore, in the second embodiment, the image processing unit 51a functions as an image processing apparatus.

The first extracting unit 513b extracts the first specific frequency component from the NB image that is the narrow band image received from the image generating unit 512 and then outputs the extracted first specific frequency component to the adding unit 518. Specifically, the first extracting unit 513b extracts, from the NB image, a high frequency component that is higher than a predetermined first threshold. More specifically, the first extracting unit 513b uses, for example, similarly to the first embodiment described above, the 3×3 high-pass filter F1; extracts, with respect to the pixel value of each of the pixels constituting the NB pixel, the high frequency component NB high of the NB image as a feature component of the NB image; and outputs the extracted high frequency component NB high to the adding unit 518.

The second extracting unit 513c extracts, with respect to a luminance component Y of the wide band image input from the first color space conversion unit 514, a second specific frequency component and then outputs the extracted second specific frequency component to the adding unit 518 and the subtracting unit 519. Specifically, the second extracting unit 513c extracts, with respect to the luminance component Y of the wide band image, the high frequency component that is higher than a predetermined second threshold. More specifically, the second extracting unit 513c uses, for example, similarly to the first embodiment described above, the 3×3 high-pass filter F1; extracts, with respect to the luminance component Y, a high frequency component Y_high of the luminance component Y of the wide band image; and outputs the extracted high frequency component Y_high to the adding unit 518 and the subtracting unit 519. Furthermore, the characteristic of the high-pass filter used by the first extracting unit 513b and the second extracting unit 513c may also be the same or may also be different with each other, but preferably have similar transmittance characteristic.

Based on the high frequency component NB_high of the NB image input from the first extracting unit 513b, based on the high frequency component Y_high of the luminance component Y of the wide band image input from the second extracting unit 513c, and based on a weighting factor α that is used at the time of adding the high frequency component NB_high to the high frequency component Y_high that are input by the input unit 52 via the control unit 54, the adding unit 518 calculates the luminance component Y'_high that is the addition component and outputs the luminance component Y'_high to the combining unit 520a. Specifically, the adding unit 518 calculates the luminance component Y'_high that is an addition component by using Equation (1) below.

$$Y\_high = \alpha \times Y\_high + (1-\alpha) \times NB\_high \quad (1),$$

where the weighting factor α is a natural number from 0 to 1.

The subtracting unit 519 calculates a low frequency component Y_low based on the luminance component Y input from the first color space conversion unit 514 and based on the high frequency component Y_high of the luminance component Y of the wide band image input from the second extracting unit 513c and then outputs the low frequency component Y_low to the combining unit 520a. Specifically, the subtracting unit 519 calculates the low frequency component Y_low that is a difference component (residual component) obtained by subtracting high frequency component Y_high of the luminance component Y of the wide band image input from the second extracting unit 513c from the luminance component Y input from the first color space conversion unit 514. More specifically, the subtracting unit 519 calculates the low frequency component Y_low by using Equation (2) below.

$$Y\_low = Y - Y\_high \quad (2)$$

The combining unit 520a calculates a luminance component Y' based on the luminance component Y° high that is an addition component input from the adding unit 518 and based on the low frequency component Y_low that is a difference component input from the subtracting unit 519 and outputs the luminance component Y' to the second color space conversion unit 516.

Process Performed by Processor

Figure 11:
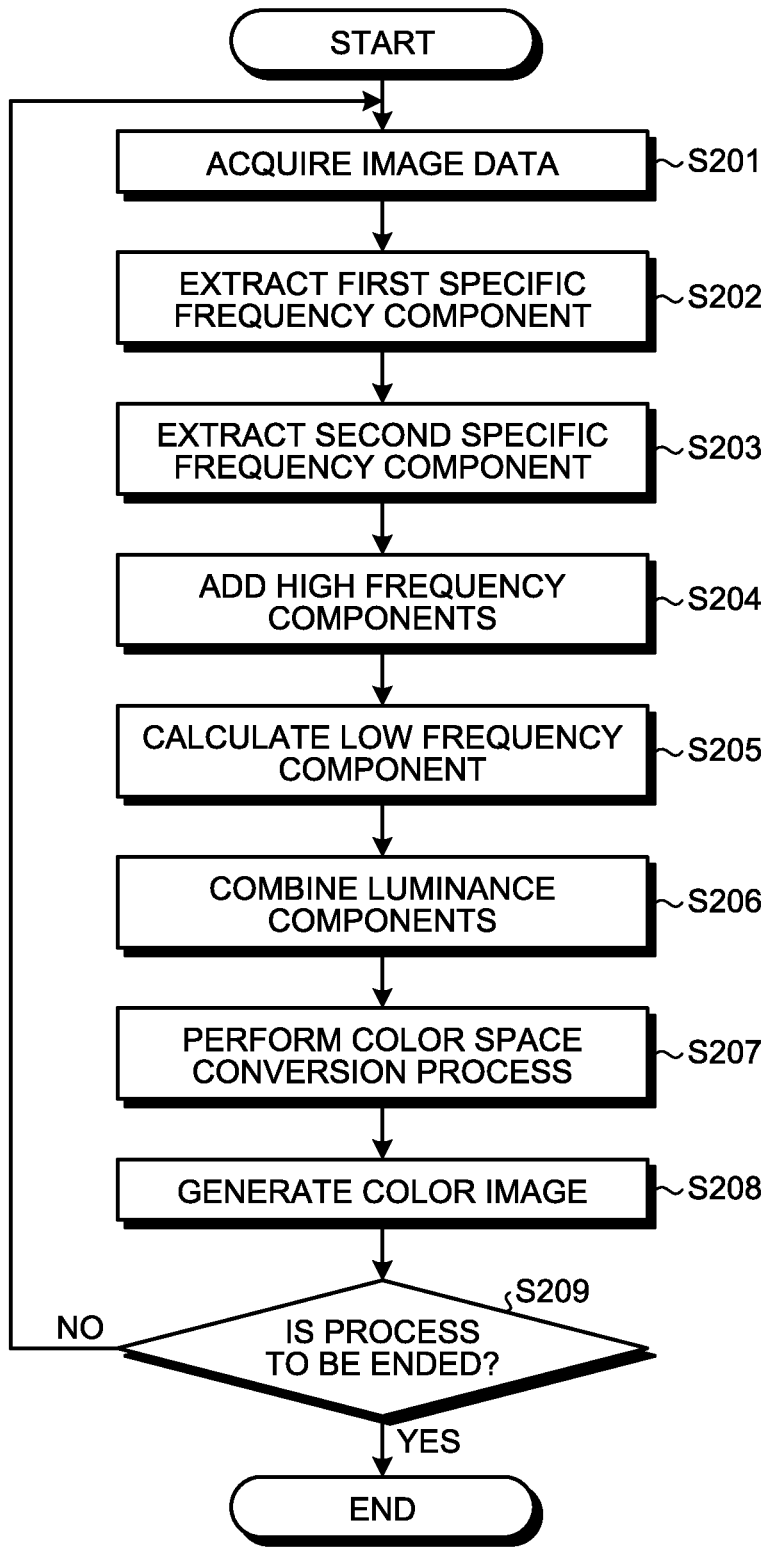
FIG. 11 is a flowchart illustrating the outline of a process performed by a processor according to the second embodiment.

In the following, the process performed by the processor 5a will be described. FIG. 11 is a flowchart illustrating the outline of the process performed by the processor 5a. In FIG. 11, Step S201 is associated with Step S101 illustrated in FIG. 7 described above.

At Step S202, the first extracting unit 513b extracts the first specific frequency component from the NB image input from the image generating unit 512. Specifically, the first extracting unit 513b extracts the high frequency component NB_high of the NB image.

Subsequently, the second extracting unit 513c extracts the second specific frequency component from the luminance component Y of the wide band image input from the first color space conversion unit 514 (Step S203). Specifically, the second extracting unit 513c extracts the high frequency component Y_high of the luminance component Y of the wide band image.

Then, the adding unit 518 calculates the luminance component Y'_high by adding, in accordance with the weighting factor α input by the input unit 52, the high frequency component NB_high of the NB image input from the first extracting unit 513b and the high frequency component Y_high of the luminance component Y of the wide band image input from the second extracting unit 513c (Step S204).

Subsequently, the subtracting unit 519 calculates the low frequency component Y_low based on the luminance component Y input from the first color space conversion unit 514 and the high frequency component Y_high of the wide band image input from the second extracting unit 513c (Step S205).

Then, the combining unit 520a calculates the luminance component Y' based on the luminance component Y'_high input from the adding unit 518 and the low frequency component Y_low input from the subtracting unit 519 (Step S206).

Step S207 to Step S209 are associated with Step S106 to Step S108, respectively, illustrated in FIG. 7 described above.

According to the second embodiment described above, even when the feature information on a special light observation image is combined with a normal light observation image, it is possible to prevent a change in the tone of the combined image.

Furthermore, in the second embodiment, the adding unit 518 calculates the luminance component Y° high of the addition component by adding, in accordance with the weighting factor α input by the input unit 52, the high frequency component NB_high of the NB image input from the first extracting unit 513b and the high frequency component Y_high of the luminance component Y of the wide band image input from the second extracting unit 513c; however, the adding unit 518 may also calculate the luminance component Y_high of the addition component by simply adding, without considering the weighting factor α, the high frequency component NB high of the NB image input form the first extracting unit 513b and the high frequency component Y_high of the luminance component Y of the wide band image input from the second extracting unit 513c.

Third Embodiment

In the following, a third embodiment will be described. An endoscope system according to the third embodiment has a configuration that is different from that of the endoscope system 1a according to the second embodiment described above. Specifically, a configuration of a processor according to the third embodiment is different from the processor 5a according to the second embodiment described above. Furthermore, the process performed by the processor in the endoscope system according to the third embodiment is different from that performed by the processor 5a according to the second embodiment. Specifically, in the second embodiment described above, the value of the weighting factor α is input via the input unit 52; however, in the third embodiment, the weighting factor α is automatically calculated. In a description below, a configuration of the endoscope system according to the third embodiment will be described and then a process performed by the processor will be described. Furthermore, components that are identical to those in the endoscope system 1a according to the second embodiment are assigned the same reference numerals and descriptions thereof will be omitted.

Configuration of Endoscope System

Figure 12:
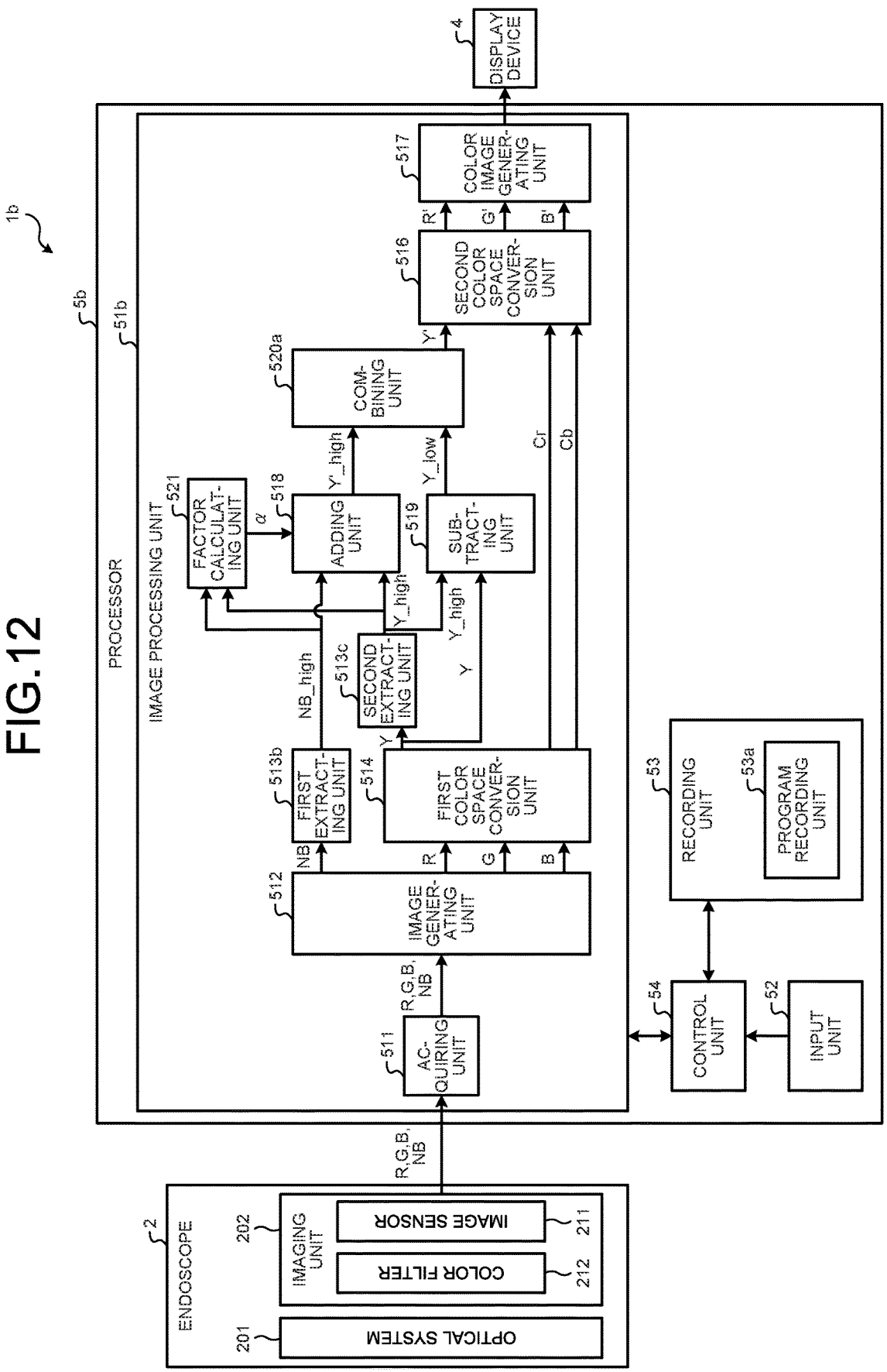
FIG. 12 is a block diagram illustrating the function of a relevant part of an endoscope system according to a third embodiment.

FIG. 12 is a block diagram illustrating a function of a relevant part of the endoscope system according to the third embodiment. An endoscope system 1b illustrated in FIG. 12 includes a processor 5b instead of the processor 5a in the endoscope system 1a according to the second embodiment described above.

Configuration of Processor

The processor 5b illustrated in FIG. 12 includes an image processing unit 51b instead of the image processing unit 51a according to the second embodiment described above.

The image processing unit 51b is constituted by using a GPU, an FPGA, or the like; acquires image data from the endoscope 2; performs predetermined image processing on the acquired image data; and outputs the processed image data to the display device 4. The image processing unit 51b further includes a factor calculating unit 521 in addition to the image processing unit 51a according to the second embodiment described above.

Based on the high frequency component NB_high(i,j) of each of the pixels in the narrow band image input from the first extracting unit 513b and based on the high frequency component Y_high(i,j) of each of the pixels in the wide band image input from the second extracting unit 513c, the factor calculating unit 521 calculates the weighting factor α that is used when the adding unit 518 adds the high frequency component NB_high of the narrow band image to the high frequency component Y_high of the wide band image.

Process Performed by Processor

Figure 13:
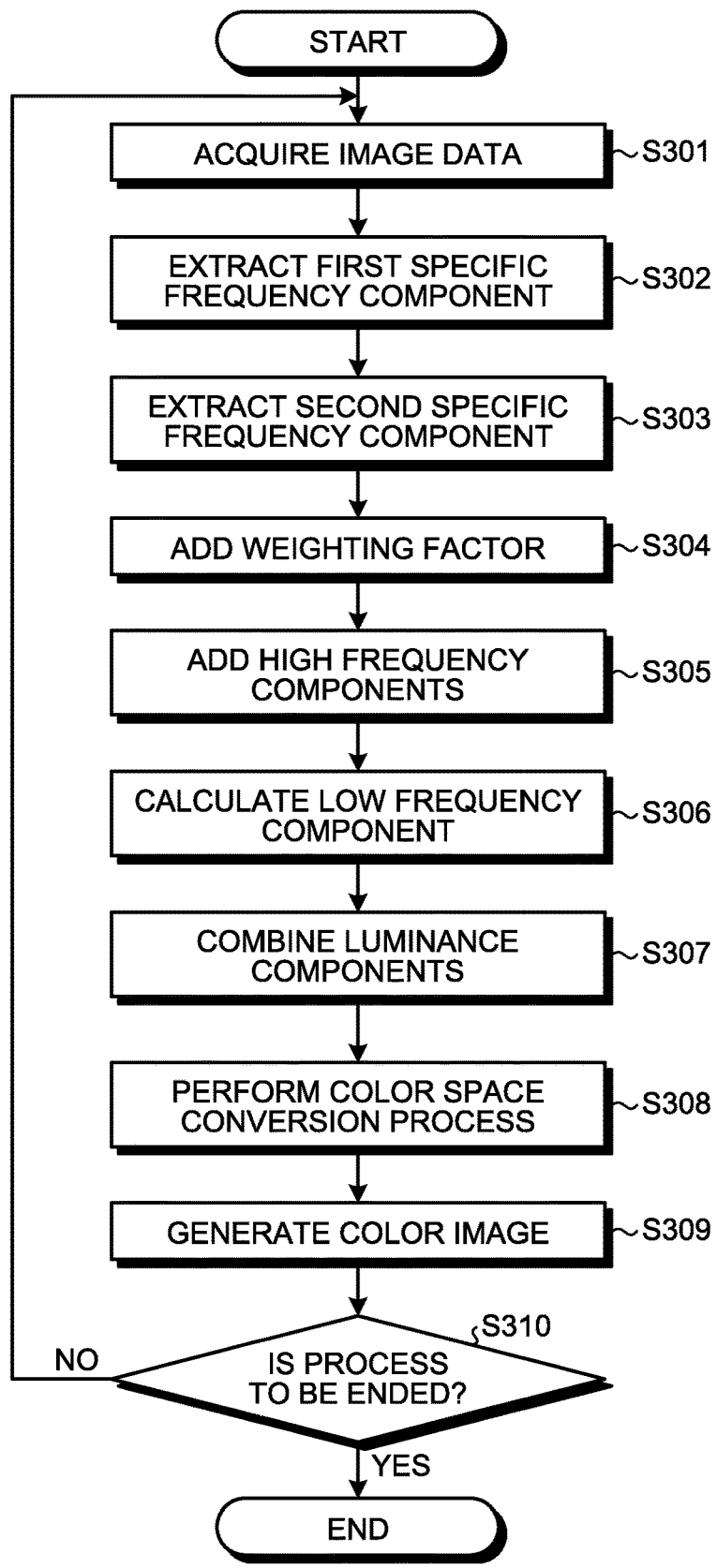
FIG. 13 is a flowchart illustrating the outline of a process performed by a processor according to the third embodiment.

In the following, the process performed by the processor 5b will be described. FIG. 13 is a flowchart illustrating the outline of the process performed by the processor 5b. In FIG. 13, Step S301 to Step S303 are associated with Step S201 to Step S203, respectively, illustrated in FIG. 11 described above.

At Step S304, the factor calculating unit 521 calculates the weighting factor α for each frame based on the high frequency component NB_high(i,j) of each of the pixels in the narrow band image input from the first extracting unit 513b and based on the high frequency component Y_high (i,j) of each of the pixels in the wide band image input from the second extracting unit 513c. Specifically, when the sum total of the high frequency component NB_high of each of the pixels in the narrow band image is denoted by Wa_NB_high and the sum total of the high frequency component Y_high of each of the pixels in the wide band image is denoted by Wa_Y_high, the factor calculating unit 521 calculates the weighting factor α by using Equations (3) to (5) below.

$$Wa\_NB\_high = \sum_{i,j} NB\_high(i, j) \quad (3)$$

$$Wa\_Y\_high = \sum_{i,j} Y\_high(i, j) \quad (4)$$

$$\alpha = \frac{Wa\_Y\_high}{Wa\_Y\_high + Wa\_NB\_high}, \quad (5)$$

where (i,j) indicates the position of a pixel.

Step S305 to Step S310 are associated with Step S204 to Step S209, respectively, illustrated in FIG. 11 described above.

According to the third embodiment described above, even when the feature information on the special light observation image is combined with the normal light observation image, it is possible to prevent a change in the tone of the combined image.

Furthermore, in the third embodiment, the factor calculating unit 521 calculates the weighting factor α for each frame based on the high frequency component NB high (i,j) of each of the pixels in the narrow band image input form the first extracting unit 513b and based on the high frequency component Y_high (i,j) of each of the pixels in the wide band image input from the second extracting unit 513c; however, the factor calculating unit 521 may also calculate the weighting factor α, for example, for each pixel. Specifically, the factor calculating unit 521 calculates the weighting factor α (i,j) by using Equation (6) below.

$$\alpha(i, j) = \frac{Y\_high(i, j)}{Y\_high(i, j) + NB\_high(i, j)} \quad (6)$$

The adding unit 518 can calculate the luminance component Y'_high(i,j) by adding, in accordance with the weighting factor α (i,j) calculated for each pixel by the factor calculating unit 521, the high frequency component NB_high(i,j) of the NB image input from the first extracting unit 513b and the high frequency component Y_high(i,j) of the luminance component Y of the wide band image input from the second extracting unit 513c.

Fourth Embodiment

In the following, a fourth embodiment will be described. The endoscope system according to the fourth embodiment has a configuration that is different from that of the endoscope system 1a according to the second embodiment described above and, furthermore, the process to be performed is different. Specifically, in the second embodiment described above, the color filter transmits a single type (1 band) of narrow band light; however, in the fourth embodiment, the color filter transmits at least two types (2 bands) of narrow band light. In a description below, a configuration of the endoscope system according to the fourth embodiment will be described and then a process performed by the processor will be described. Furthermore, components that are identical to those in the endoscope system 1a according to the second embodiment are assigned the same reference numerals and descriptions thereof will be omitted.

Configuration of Endoscope System

Figure 14:
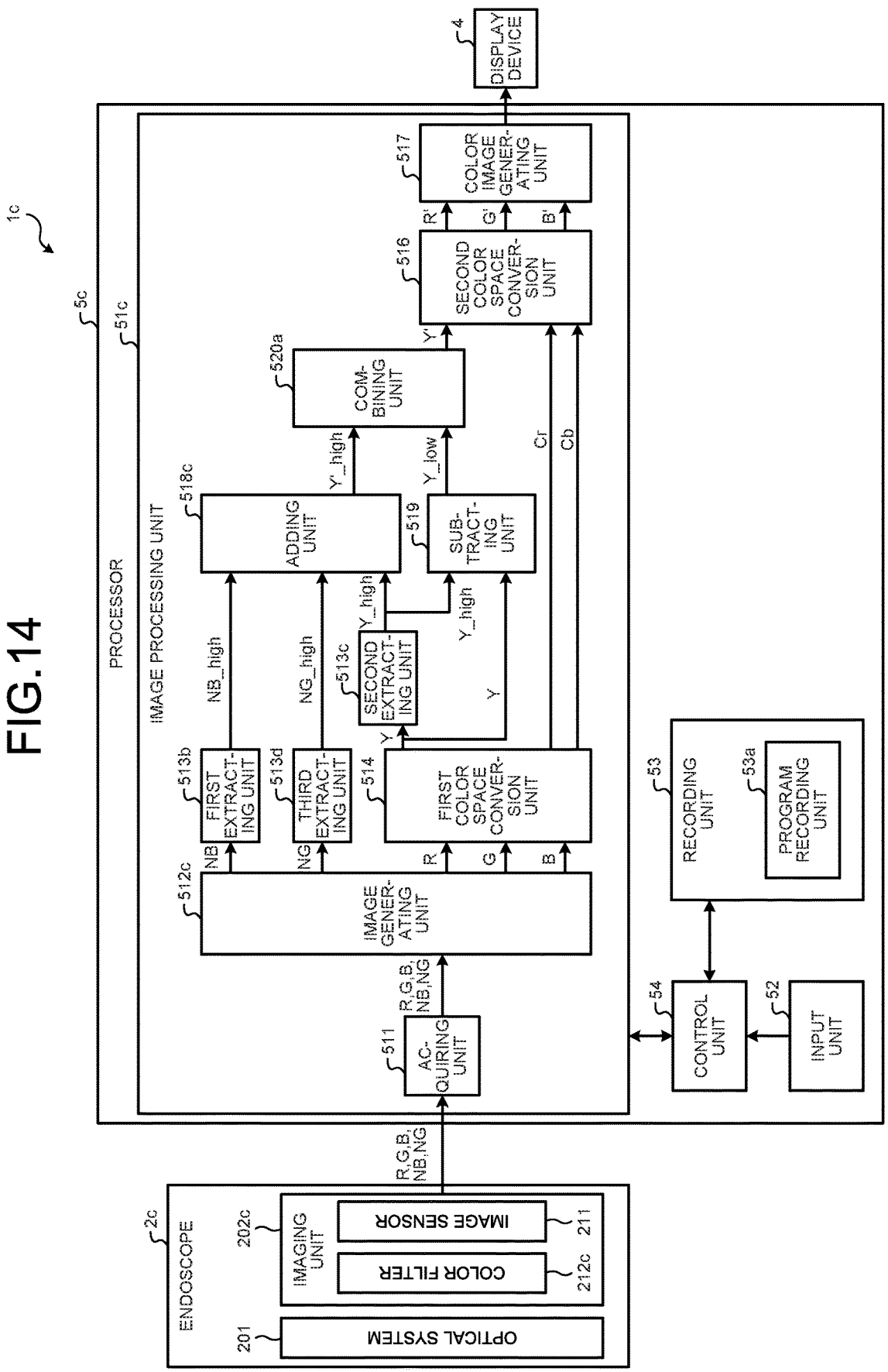
FIG. 14 is a block diagram illustrating the function of a relevant part of an endoscope system according to a fourth embodiment.

FIG. 14 is a block diagram illustrating a function of a relevant part of the endoscope system according to the fourth embodiment. An endoscope system 1c illustrated in FIG. 14 includes an endoscope 2c and a processor 5c instead of the endoscope 2 and the processor 5a, respectively, included in the endoscope system 1a according to the second embodiment described above.

Configuration of Endoscope

First, a configuration of the endoscope 2c will be described.

The endoscope 2c includes an imaging unit 202c instead of the imaging unit 202 in the endoscope according to the second embodiment described above. The imaging unit 202c includes a color filter 212c instead of the color filter 212 according to the second embodiment described above.

The color filter 212c is formed by using a filter unit that includes a wide-band filter R that transmits light having a red wavelength band, a wide-band filter G that transmits light having a green wavelength band, a wide-band filter B that transmits light having a blue wavelength band, a narrow-band filter NB that transmits light having a wavelength band that is the blue wavelength band and that is narrower than the blue wavelength band, and a narrow-band filter NG that transmits light having a wavelength band that is a green wavelength band and that is narrower than the green wavelength band. The color filter 212c is formed by arranging the filter unit so as to be associated with the pixels of the image sensor 211.

Figure 15:
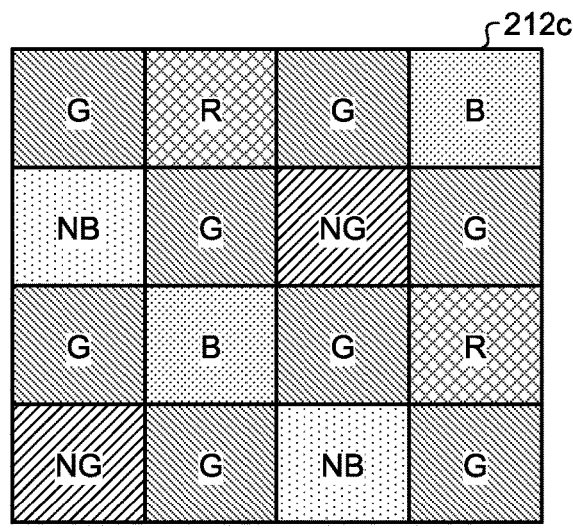
FIG. 15 is a diagram schematically illustrating a configuration of a color filter according to the fourth embodiment.

FIG. 15 is a diagram schematically illustrating a configuration of the color filter 212c. As illustrated in FIG. 15, the color filter 212c is formed by using a filter unit formed of a predetermined array pattern that has, as a single set, two wide-band filters R each of which transmits a red component, eight wide-band filters G each of which transmits a green component, two wide-band filters B each of which transmits a blue component, two narrow-band filters NB each of which transmits light having a narrow band, and two narrow-band filters NG each of which transmits light having a wavelength band narrower than the green wavelength band. The color filter 212c is arranged at the position associated with one of the plurality of pixels of the image sensor 211 in which each of the filters forming the array pattern described above are two dimensionally arrayed.

Figure 16:
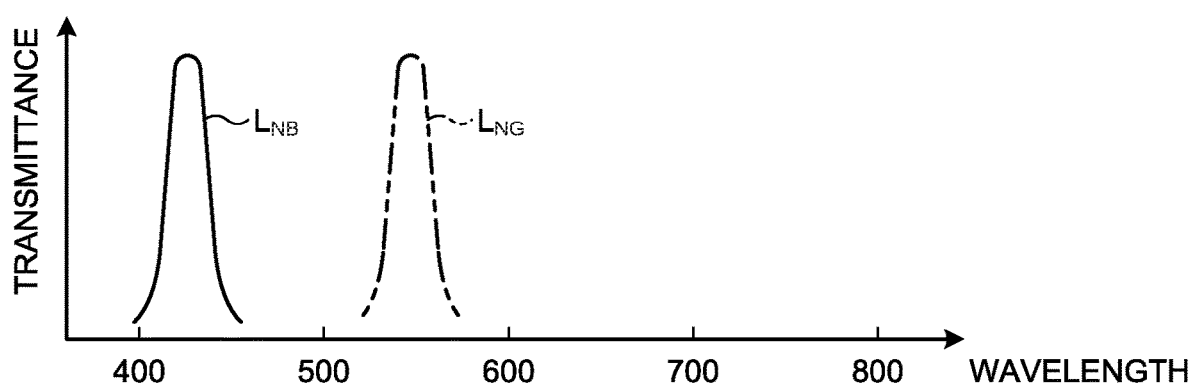
FIG. 16 is a diagram illustrating the relationship between the transmittance and the wavelength of a narrow-band filter NB and a narrow-band filter NG constituting a color filter according to the fourth embodiment.

FIG. 16 is a diagram illustrating the relationship between the transmittance and the wavelength of the narrow-band filter NB and the narrow-band filter NG constituting the color filter 212c. In FIG. 16, the horizontal axis represents the wavelength (nm) and the vertical axis represents the transmittance. Furthermore, in FIG. 16, a curve $L_{NB}$ represents the relationship between the transmittance and the wavelength of the narrow-band filter NB and a curve $L_{NG}$ represents the relationship between the transmittance and the wavelength of the narrow-band filter NG. Furthermore, in FIG. 16, a description will be given of a case in which the peak wavelength of the narrow-band filter NB is in the range between 390 nm and 445 nm and the peak wavelength of the narrow-band filter NG is in the range between 530 nm and 550 nm.

As illustrated in FIG. 16, the spectral characteristic of the narrow-band filter NB is that the wavelength band thereof is included in the wavelength band of the wide-band filter B and is narrower than that of the wide-band filter B. Furthermore, the spectral characteristic of the narrow-band filter NG is included in the wavelength band of the wide-band filter G and in the wavelength band narrower than that of the wide-band filter G. Furthermore, in a description below, the pixels formed by arranging the narrow-band filter NG are referred to as an NG pixel.

Configuration of Processor

In the following, a configuration of the processor 5c will be described.

The processor 5c illustrated in FIG. 14 includes an image processing unit 51c instead of the image processing unit 51a in the processor 5a according to the second embodiment described above. The image processing unit 51c further includes a third extracting unit 513d in addition to the image processing unit 51b.

An image generating unit 512c performs, based on the pixel value of each of the pixels (each channel) that have been input from the acquiring unit 511, a known demosaicing process for interpolating the pixel value of the pixel in which the pixel value has been lost, whereby the image generating unit 512c generates each of an R image (first interpolation image data), associated with light having a red wavelength band, a G image (second interpolation image data) associated with light having a green wavelength band, a B image (third interpolation image data) associated with light having a blue wavelength band, an NB image (fourth interpolation image data) associated with narrow band light, and an NG image (fifth interpolation image data) associated with narrow band light. The image generating unit 512c outputs the R image, the G image, and the B image to the first color space conversion unit 514 and, furthermore, outputs the NB image to each of the first extracting unit 513b and the NG image to the third extracting unit 513d.

The third extracting unit 513d extracts a specific frequency component from the NG image input from the image generating unit 512c and outputs the extracted specific frequency component to an adding unit 518c. Specifically, the third extracting unit 513d extracts a high frequency component that is higher than a predetermined threshold from the NG image. More specifically, the third extracting unit 513d uses, for example, a 3×3 high-pass filter; extracts, with respect to the pixel value of each of the pixels constituting the NG image, the high frequency component NG_high of the NG image as the feature component of the NG image and outputs the high frequency component NG high to the adding unit 518c.

The adding unit 518c calculates the luminance component Y'_high based on the high frequency component NB_high of the narrow band image NB, the high frequency component NG_high of the narrow band image NG, the high frequency component Y_high of the wide band image, and the weighting factors α and β that are input via the input unit 52. Specifically, the adding unit 518c calculates the luminance component Y'_high by using Equation (7) below.

$$Y'\_high=(1-\alpha-\beta)Y\_high+\alpha \times NB\_high+\beta \times NG\_high \quad (7)$$

Process Performed by Processor

Figure 17:
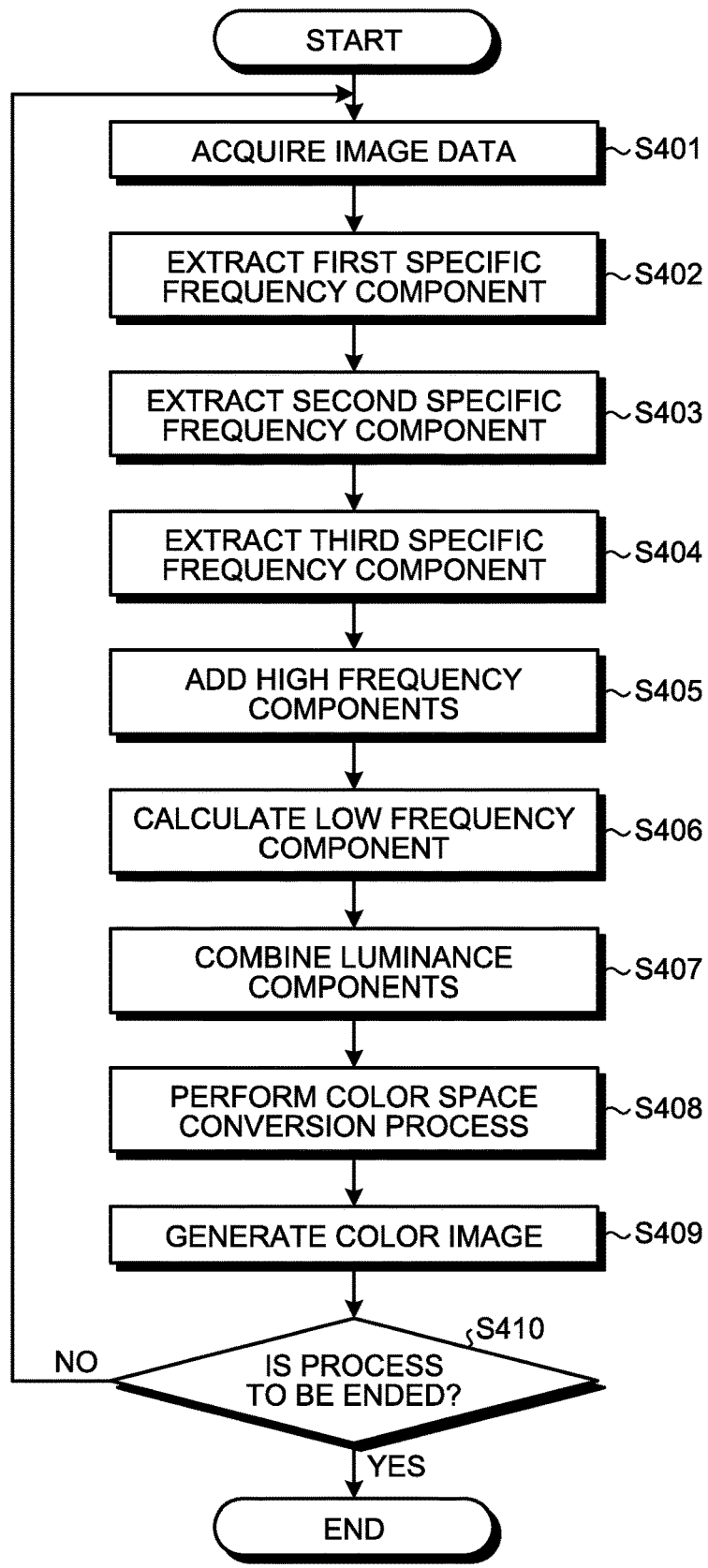
FIG. 17 is a flowchart illustrating the outline of a process performed by a processor according to the fourth embodiment.

In the following, the process performed by the processor 5c will be described. FIG. 17 is a flowchart illustrating the outline of the process performed by the processor 5c. In FIG. 17, Step S401 to Step S403 are associated with Step S301 to Step S303, respectively, illustrated in FIG. 13 described above.

At Step S404, the third extracting unit 513d extracts the third specific frequency component from the NG image input from the image generating unit 512c. Specifically, the third extracting unit 513d uses, for example, a 3×3 high-pass filter; extracts, with respect to the pixel value of each of the pixels constituting the NG image, the high frequency component NG_high of the NG image as the feature component of the NG image; and outputs the high frequency component NG high to the adding unit 518c.

Step S405 to Step S410 are associated with Step S305 to Step S310, respectively, illustrated in FIG. 13 described above.

According to the fourth embodiment described above, even when the feature information on a special light observation image is combined with a normal light observation image, it is possible to prevent a change in the tone of the combined image.

Other Embodiments

Furthermore, in the first to the fourth embodiments, in the endoscope systems 1 and 1a to 1c, each of the endoscopes 2 and 2c, the display device 4, the recording unit 53, and the control unit 54 are provided; however, these components may also be omitted as long as they do not depart from the spirit. Furthermore, various modifications may be made by appropriately combining a plurality of components disclosed in the first to the fourth embodiments described above. For example, some components may also be omitted from all of the components described above in the first to the fourth embodiments. Furthermore, the components described in the first to the fourth embodiments described above may also be appropriately combined.

Furthermore, in the embodiments, the "components" described above can be read as "means", "circuits", or the like. For example, a control unit can be read as a control means or a control circuit.

Furthermore, in the embodiments, the input/output has been described by using RGB colors (primary colors); however, the colors are not limited thereto and CMY colors (complementary color) may also be used for the input/output.

Furthermore, in the embodiments, image data is transmitted to the image processing apparatus via a transmission cable; however, for example, the image data does not always need to be transmitted in a wired manner but may also be wirelessly transmitted. In this case, image data or the like may also be transmitted to the image processing apparatus in accordance with a predetermined wireless communication standard (for example, Wi-Fi (registered trademark) or Bluetooth (registered trademark)). Of course, radio communication may also be performed in accordance with another radio communication standard.

Furthermore, in the embodiments, the light source device and the image processing apparatus (processor) are separately constituted; however, the configuration is not limited to this. For example, it is also possible to use a configuration in which the image processing apparatus and the light source device are integrally constituted.

Furthermore, in the embodiments, a synchronous endoscope has been described as an example; however, a frame-sequential endoscope may also be used. Furthermore, in the embodiments, in addition to narrow band light, it is also possible to use an endoscope capable for irradiating predetermined narrow band light. Furthermore, in the embodiments, in addition to a rigid endoscope, it is also possible to use a flexible endoscope (upper/lower endoscope), a sinus endoscope, and a capsule endoscope.

Furthermore, in the embodiments, an endoscope inserted into a subject has been used; however, for example, a capsule endoscope or an imaging device that captures images of the subject may also be used.

Furthermore, in the explanation of the flowcharts described in the application, the relationship between before and after the processes performed at each step is stated by using "first", "then", "subsequently", and the like; however, the order of the processes needed to implement the present disclosure is not uniquely determined by the descriptions above. Specifically, the order of the processes in the flowcharts described in the application may also be changed as long as processes do not conflict with each other.

According to the present disclosure, an advantage is provided in that even when the feature information on a special light observation image is combined with a normal light observation image, it is possible to prevent a change in the tone of the combined image.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   a processor comprising hardware, the processor being configured to execute:
   acquiring image data generated by an image sensor formed by a predetermined array pattern using a first pixel that receives light having a red wavelength band, a second pixel that receives light having a green wavelength band, a third pixel that receives light having a blue wavelength band, and a fourth pixel that receives narrow band light having a wavelength band that is narrower than at least any of the red, green, and blue wavelength bands;
   generating, by performing a demosaicing process for interpolating a pixel value on the acquired image data, first interpolation image data associated with the light having the red wavelength band, second interpolation image data associated with the light having the green wavelength band, third interpolation image data associated with the light having the blue wavelength band, and fourth interpolation image data associated with the narrow band light;
   performing a color space conversion process for converting each of the first interpolation image data, the second interpolation image data, and the third interpolation image data to a luminance component and a color difference component;
   extracting a first specific frequency component included in the fourth interpolation image data;
   combining the converted luminance component with the extracted first specific frequency component; and
   generating color image data based on a combination result obtained by the combining and based on the color difference component,
   wherein the processor extracts, as the first specific frequency component, a high frequency component that is higher than a predetermined first threshold,
   wherein the processor further executes:
   extracting a second specific frequency component included in the luminance component;
   calculating a difference component by subtracting the extracted second specific frequency component from the luminance component; and
   calculating an addition component by adding the extracted first specific frequency component to the extracted second specific frequency component, and
   wherein the combining combines the calculated difference component with the calculated addition component.

2. The image processing apparatus according to claim 1, wherein the processor extracts a high frequency component that is higher than a predetermined second threshold as the first specific frequency component or the second specific frequency component.

3. The image processing apparatus according to claim 2, further comprising an input device that receives an input of a weighting factor that is used when the first specific frequency component and the second specific frequency component are added,
   wherein the processor calculates the addition component by adding the first specific frequency component to the second specific frequency component in accordance with the weighting factor.

4. The image processing apparatus according to claim 2, wherein the processor further executes calculating a weighting factor that is used when the first specific frequency component and the second specific frequency component are added based on the first specific frequency component and the second specific frequency component, and
   the processor calculates the addition component by adding the first specific frequency component to the second specific frequency component in accordance with the weighting factor.

5. An image processing method performed by an image processing apparatus, the image processing method comprising:
   acquiring image data generated by an image sensor formed by a predetermined array pattern using a first pixel that receives light having a red wavelength band, a second pixel that receives light having a green wavelength band, a third pixel that receives light having a blue wavelength band, and a fourth pixel that receives narrow band light having a wavelength band that is narrower than at least any of the red, green, and blue wavelength bands;
   generating, by performing a demosaicing process for interpolating a pixel value on the acquired image data, first interpolation image data associated with the light having the red wavelength band, second interpolation image data associated with the light having the green wavelength band, third interpolation image data associated with the light having the blue wavelength band, and fourth interpolation image data associated with the narrow band light;
   performing a color space conversion process for converting each of the first interpolation image data, the second interpolation image data, and the third interpolation image data to a luminance component and a color difference component;
   extracting, as a first specific frequency component included in the fourth interpolation image data, a high frequency component that is higher than a predetermined first threshold;
   combining the converted luminance component with the extracted first specific frequency component;
   generating color image data based on a combination result obtained by the combining and based on the color difference component;
   extracting a second specific frequency component included in the luminance component;
   calculating a difference component by subtracting the extracted second specific frequency component from the luminance component; and calculating an addition component by adding the extracted first specific frequency component to the extracted second specific frequency component, and wherein the combining combines the calculated difference component with the calculated addition component.

6. A non-transitory computer readable recording medium on which an executable program is recorded, the program instructing a processor of an image processing apparatus to execute:

acquiring image data generated by an image sensor formed by a predetermined array pattern using a first pixel that receives light having a red wavelength band, a second pixel that receives light having a green wavelength band, a third pixel that receives light having a blue wavelength band, and a fourth pixel that receives narrow band light having a wavelength band that is narrower than at least any of the red, green, and blue wavelength bands;

generating, by performing a demosaicing process for interpolating a pixel value on the acquired image data, first interpolation image data associated with the light having the red wavelength band, second interpolation image data associated with the light having the green wavelength band, third interpolation image data associated with the light having the blue wavelength band, and fourth interpolation image data associated with the narrow band light;

performing a color space conversion process for converting each of the first interpolation image data, the second interpolation image data, and the third interpolation image data to a luminance component and a color difference component;

extracting, as a first specific frequency component included in the fourth interpolation image data, a high frequency component that is higher than a predetermined first threshold;

combining the converted luminance component with the extracted first specific frequency component;

generating color image data based on a combination result obtained by the combining and based on the color difference component;

extracting a second specific frequency component included in the luminance component;

calculating a difference component by subtracting the extracted second specific frequency component from the luminance component; and calculating an addition component by adding the extracted first specific frequency component to the extracted second specific frequency component, and wherein the combining combines the calculated difference component with the calculated addition component.

* * * * *